US007848936B2

(12) United States Patent
Glaser-Seidnitzer et al.

(10) Patent No.: US 7,848,936 B2
(45) Date of Patent: Dec. 7, 2010

(54) METHOD FOR PROVIDING UPDATED PROTOCOLS IN A MEDICAL RADIOLOGY INFORMATION SYSTEM

(75) Inventors: Karlheinz Glaser-Seidnitzer, Fürth (DE); Thomas Mangold, Neunkirchen am Brand (DE); Elmar Seeberger, Weissenburg (DE)

(73) Assignee: Siemens Aktiengesellschaft, Munich (DE)

( * ) Notice: Subject to any disclaimer, the term of this patent is extended or adjusted under 35 U.S.C. 154(b) by 555 days.

(21) Appl. No.: 11/683,088

(22) Filed: Mar. 7, 2007

(65) Prior Publication Data
US 2007/0211756 A1 Sep. 13, 2007

(30) Foreign Application Priority Data
Mar. 7, 2006 (DE) ........................ 10 2006 010 535

(51) Int. Cl.
*G06Q 10/00* (2006.01)
*G06Q 50/00* (2006.01)
*G06F 15/16* (2006.01)

(52) U.S. Cl. ......................................................... 705/2

(58) Field of Classification Search ..................... 705/2, 705/3; 709/201, 203; 370/466
See application file for complete search history.

(56) References Cited

U.S. PATENT DOCUMENTS

| 6,260,065 | B1 * | 7/2001 | Leiba et al. ................. 709/224 |
| 6,272,469 | B1 * | 8/2001 | Koritzinsky et al. ............ 705/2 |
| 6,311,278 | B1 * | 10/2001 | Raanan et al. ................. 726/14 |
| 6,774,371 | B2 * | 8/2004 | Garrard et al. ......... 250/363.08 |
| 2005/0234325 | A1 | 10/2005 | Hofmann et al. |

* cited by examiner

*Primary Examiner*—Gerald J. O'Connor
*Assistant Examiner*—Neha Patel
(74) *Attorney, Agent, or Firm*—Schiff Hardin LLP

(57) ABSTRACT

In a method, a device and a computer program product for provision of protocols for configuration of a medical apparatus in the framework of a medical examination, the protocols are decentrally generated at a medical apparatus and are relayed to a central radiology information system. From the central RIS server the modified protocol can be relayed to arbitrary further instances via a network. The method employs a consistency mechanism which ensures that a set of protocols remains consistent and uniform given changes of one protocol.

6 Claims, 2 Drawing Sheets

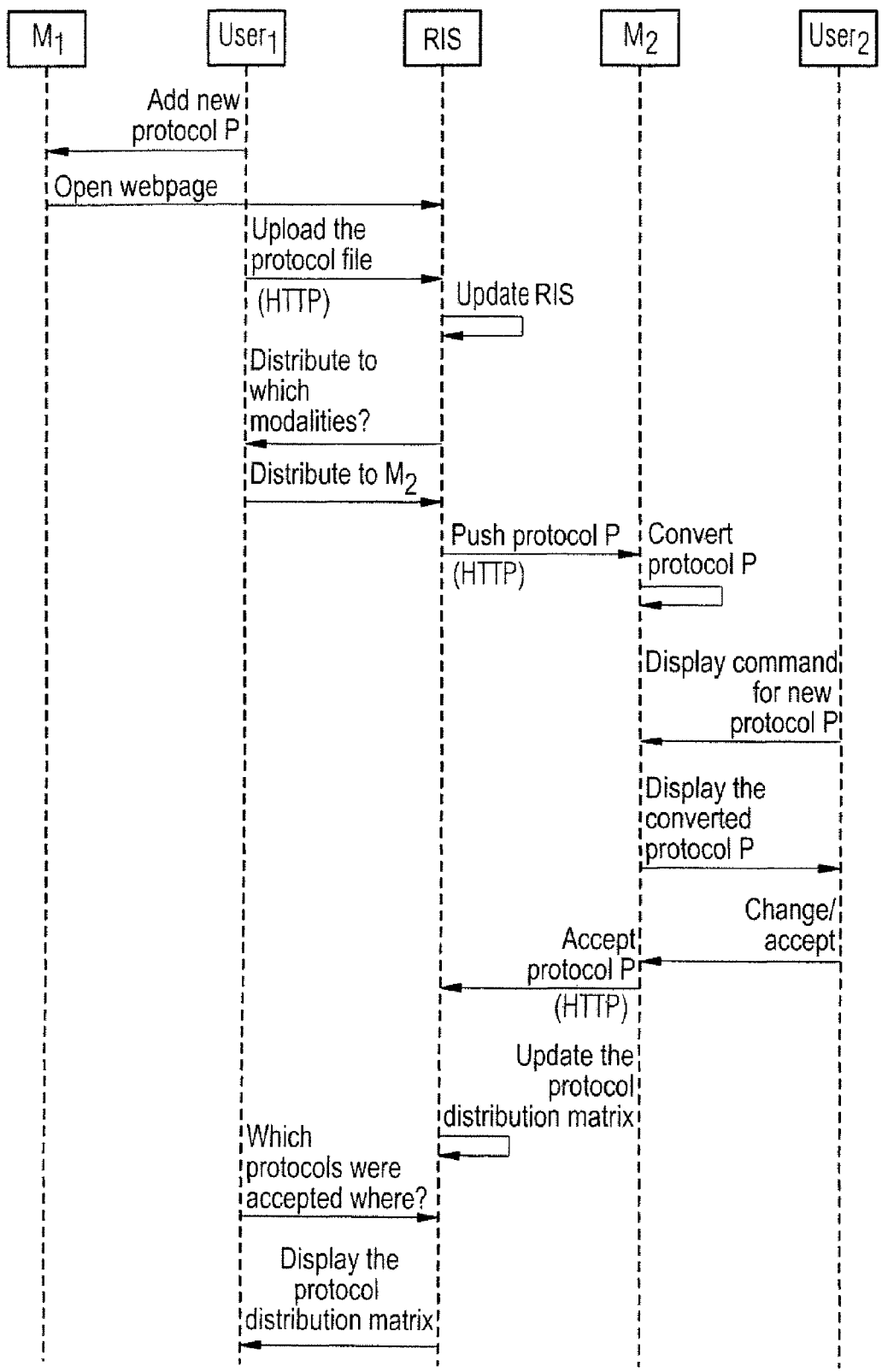

METHOD FOR PROVIDING UPDATED PROTOCOLS IN A MEDICAL RADIOLOGY INFORMATION SYSTEM

BACKGROUND OF THE INVENTION

1. Field of the Invention

The present invention concerns a method, a device and a system for automatic upload and/or download of protocols in the environment of a radiology information system (designated as an RIS for short in the following).

2. Description of the Prior Art

A number of medical-technical apparatuses, or also known as modalities, that serve for implementation of a medical examination are connected to an RIS system. The apparatuses can be, for example, MR apparatuses. It is necessary for these to be configured or set with a number of parameters for best usage. These settings concern, for example, data acquisition instructions for the apparatus. All settings that concern an application and/or an application case are included in a protocol.

Established radiology departments today are normally optimally designed as computer-controlled, which leads to the situation that the data are exchanged via a network. In such a network the RIS system is typically fashioned as a central node that engages in data exchange or interacts with further nodes via corresponding network connections, for example via HTTP transactions. The nodes can be modalities of different types, further RIS systems or different computer-controlled instances for data processing of medical data. In the context of this data processing it is necessary to bring the protocols forming the basis for this processing up to the most recent state and to update them. It must be ensured that the newest version of the protocols is used.

In conventional procedures known in the prior art updates of a protocol at the respective modalities was executed manually and decentrally. This normally ensues by an employee of the department having the current protocols on a portable data medium (such as, for example, on a diskette or a memory stick) and copying the data from the data medium to the modality. This previous procedure has proven to be very time and labor intensive. Moreover, this procedure can easily lead to errors that arise due to incorrect inputs, and inconsistent data sets may possibly be generated because, for example, not all modalities have been supplied with the same current version of protocols.

SUMMARY OF THE INVENTION

An object of the present invention is to avoid the aforementioned conventional procedure.

The invention concerns an improved detection, forwarding and provision of these protocols within the RIS system.

More specifically, the present invention provides a method with which an upload and/or a download of protocols for configuration of medical-technical apparatuses in a medical radiology information system can be automated, centralized and simplified.

This object also is achieved by a device as well as a computer program product for provision of protocols for setting of a medical examination apparatus.

In the following the invention is described based on the solution according to the method. The described advantages, embodiments and features are equally applicable to the other inventive solutions as well as to the device and the product.

The above object is achieved by a method for provision of protocols for configuration of a medical system for implementing a medical examination, the medical apparatus having at least one central information system (that can function as a server) and a number of apparatuses and/or modalities for implementation of the medical examination (the modalities function as a server client), wherein the information system, the modalities and possibly further nodes interact via a network, and in which the protocol is generated at one modality and relayed to the information system for provision of the respective protocol.

In the preferred embodiment, the protocols are of the type that are relevant in the framework of a magnetic resonance examination (MR examination). The invention is, however, not limited to this and can likewise be applied to other medical examinations (such as, for example, to CT examinations, ultrasound or other examinations at medical-technical apparatuses) that require relatively complex and comprehensive settings.

As used herein the term "protocol" encompasses properties, parameters and/or other settings for the respective examination modality. These are advantageously MR protocols, contrast agent information, other configurable information (such as, for example, an echo time etc.) or settings that concern the respective modality, parameters that relate to the software of the modality or measurement instructions. A protocol is typically dependent on the respective modality and/or on the respective execution apparatus. Moreover, a modality can be operated by different software tools. In this case a protocol is likewise dependent on these software products.

In the framework of this invention, the term "medical apparatus" encompasses a technical apparatus that is used in the framework of a medical examination of a patient. In the preferred embodiment it is an MR apparatus. It is likewise possible to incorporate further apparatuses into a more complex system or to use alternative apparatuses such as, for example, CT apparatuses, ultrasound apparatuses, x-ray systems or the like. The medical apparatuses normally exhibit a relatively comprehensive and complex configuration profile. In other words, it is necessary to implement a number of parameters and settings in order to produce the desired results with the apparatus, in particular the images with the desired quality, or with the desired parameters (such as resolution, contrast, selection of the section, size, etc.). The modalities are thus typically medical apparatuses. It is likewise possible to use other technical apparatuses that can be relevant in the framework of the medical examination. These can be complex apparatuses or systems as well as small instruments or equipment. It is likewise possible to use further or alternative apparatuses that merely exhibit a specific functionality such as, for example, apparatuses that are used for the transport or the movement of the patient, apparatuses that serve for administration of the computer system or of the network, or other hardware or software tools.

The inventive method is based on a central information system that, in the preferred embodiment, is fashioned as an RIS system. It can be a central information-technology node in a radiology department, into which all information about the connected modalities is entered and (if applicable) processed or is relayed to further components for further processing. There is thereby a large share of data that are available to the RIS system and that must be distributed to other modalities for further processing.

A network is provided in order to ensure the data exchange between the respective connected components, in particular between the respective modalities and the RIS system. The type of the network (local area network—LAN or wide area network—WAN), the design of the network (in particular the protocol for the data exchange), the extent or other parameters are freely selectable. In the preferred embodiment the HTTP protocol is used. The modalities (in particular a magnetic resonance apparatus or the like) generate the specific data set (in particular documents and associated files such as images, etc.) and forward the data to a memory of the RIS system in order to enable a later processing of the data. It is also possible to store the data sets in the RIS system and to relay the data to other modalities or components. The modalities access the RIS server via a URL address.

The use of the HTTP protocol is not mandatory for the execution of the inventive solution, but the use of this protocol has proven to be advantageous because many tools and systems already in use are based on this protocol, so that it allows the system to interact very flexibly with other systems. Moreover, it can be expanded relatively easily.

As noted above, a problem of conventional systems in the prior art is the MR protocols with the relevant configuration pattern recognition algorithms for the setting of the respective modality or the medical apparatus had to be executed separately, decentrally and manually by a service technician. This typically occurred by setting a specific MR protocol, which had proven to be advantageous for a particular application, in a specific modality. For example, specific contrasts, color settings, storage information etc. can be stored. As already mentioned, such data were typically stored as a protocol on a portable data medium. It was necessary for the service technician to physically proceed to all other modalities that are connected to the RIS system and also upload the respective MR protocol to these modalities. This procedure is disadvantageously very time-intensive and moreover error-prone, since a data loss and/or incorrect inputs cannot be precluded. A further, very significant disadvantage is that inconsistent data sets with regard to the MR protocols between the respective modalities cannot be precluded. This can lead to serious errors since, for example, two different modalities of the identical category, which should be configured with the same MR protocol parameters, are configured with different protocol parameters.

In order to avoid the disadvantages mentioned in the preceding, in accordance with the invention the procedure is standardized and automated so that a manual upload of the relevant data sets to the modalities on site is no longer necessary. A further, very significant advantage of the inventive solution is that the protocol-relevant data sets can be processed at a central location. It is thereby possible to achieve control on a central plane for configuration of the respective modalities. An unintentional overwriting of previously-used protocols can thereby be safely avoided. When, for example, a specific protocol has proven to be reasonable for a specific medical examination at a modality, it is frequently (however not always) reasonable to also provide this protocol data set to other modalities and to bring it into use. However, there can be exceptional cases in which the previous setting parameters of the respective modality should not be overwritten. These exception conditions are typically also stored in the central control system. If the central control system now receives the task to transfer a specific protocol created at a specific modality to other modalities, this task is first subjected to a check. In particular the exception conditions mentioned in the preceding are reviewed in this check. In an embodiment of the invention, all control information already exists in the monitoring system. The monitoring task (in particular for the overwriting of already-existing protocols) thus can be executed entirely automated. However, all information is typically not present in digital form, so a user confirms the respective task for overwriting of an existing protocol and/or the monitoring task as allowed or not by a user interaction via an interface.

In the preferred embodiment the data exchange between a respective modality and the central information system occurs in a bidirectional manner. In other words, protocol data sets that have been recorded at a modality are transmitted to the central information system. Moreover, these transmitted protocol data sets are relayed from the central information system (which can also function as a server) to the respective selected and relevant modalities in order to supply these with the configuration parameters. In an alternative embodiment of the invention for security reasons that this data exchange is not designed to be bidirectional (as in the preceding), but rather only one communication direction is provided. This requires that the other communication direction be conducted by a manual transfer of the data. In other words, the respective modalities that are connected to the information system are equipped with a unit that enables a download and/or an upload of protocol-related data (in particular protocol codes) of the radiology information system via a network access. The radiology information system functions as a server and stores a database of procedures and protocol coding schemes. The central information system or the server provides a database of procedures that respectively serve for distribution of the respective data sets to the connected modalities. In reverse, the modalities or the respective clients connected to the network can supply the RIS databank with the current data sets for their local database, or they can replay new data sets that are related to the protocol to the RIS server.

In the preferred embodiment a protocol identifier is respectively associated with each protocol. This association is advantageously a one-to-one association, such that it is possible to simply identify the respective protocol using the protocol identifier.

According to a preferred embodiment, the inventive method employs an association mechanism that is designed to associate a specific modality with the protocol designed in an optimal manner for it, or if applicable, a series of protocols that are sequentially executed. In this embodiment the association mechanism is designed for different application situations, such that the criteria on which the association mechanism is based can be dynamically configured by the user. For example, through the association mechanism it is set whether an already-existing protocol can simply be overwritten by a new protocol, or whether further checks are necessary for this. Moreover, it can be set how long a selected protocol should be valid for the respective modality (determination of the validity duration).

An important feature of the invention is that the data set of the protocols that are centrally held in the information system are reliably consistent. A consistency mechanism is therefore accessed that is designed so that the set of protocols stored in the central information system remains uniform given a change of one protocol. It can thereby be ensured that all protocol instances are redone given a protocol change. It is thus not possible that the same protocol can exist with different protocol contents. This feature can clearly increase the security of the system overall.

The inventive method employs a user interface via which an exchange (in particular a download and/or an upload of protocols) is controlled and/or executed. Via this user interface it is also possible for a user to receive information about a currently loaded protocol and/or to modify it according to configurable criteria.

The user interface can employ a specific modification interface using which an already-existing protocol for a respective modality can be modified as needed according to configurable parameters. It is possible for the user to select the configuration parameters that he or she wants to change by a specific user interaction (mouse click, keyboard input etc.). If applicable, the user can receive supplementary information (help information) for this purpose. After changing these configuration parameters the user is asked whether he or she would like to retain and save the changed settings. In the case of affirmation this changed protocol data set is forwarded to the central RIS system. At a central location it can then be decided whether the changed protocol data set should also be transferred to further modalities for further use.

In order to increase the security of the overall system, a warning message is output for all changes that should be made to the protocol-related data sets, in the event that the changes lead to an overwriting of already-existing data sets. The danger of an unintended overwrite thus can be reduced.

According to the invention the protocol contents at the modality are apparatus-dependent and/or dependent on the software with which the modality is operated. This is a significant difference compared to the previously-existing protocol coding schemes that are configured at the central RIS system.

Through the configuration of the association mechanism it is possible to cover different application cases and to flexibly supply the modalities with the respective protocols. It is thus possible to also relay the same protocol code as needed to different modalities or to modalities of different types in the event that this is desirable for the overall functionality of the system.

The parameters based on which it is decided which protocol is optimally adapted for the respective modality are typically provided or determined by the specific modality. In an alternative embodiment, the association mechanism is centrally controlled by the RIS system. In this case the parameters on which the association mechanism is based, and a protocol associated with the modality are controlled by the central RIS system. Furthermore, the modality accepts the protocols determined for it and provided by the central RIS system. This can ensue by a suitable input on a user interface.

In order to provide an optimized administration of the protocols, the inventive method allows access to a specific data structure in which a consistent set of available protocols is stored in the form of a tree structure. A protocol typically includes a series of commands. These commands can be measurement instructions, steps in the framework of an apparatus operation, settings of the apparatus or other specifications in the framework of the preparation of a medical examination. In addition to planned execution steps, requested execution steps of a protocol are typically stored. The same protocol can occur multiple times within the structured examination tree. The content of such an examination tree is determined specifically for each modality in accordance with the invention. This typically ensues centrally via the RIS system.

It is important that a determined protocol can respectively be accessed via a protocol identifier. It is thereby insignificant whether the name of the respectively protocol is uniform or not. In some cases the name of a protocol is language-dependent, but the name normally can be used as an additional identifier for the protocol files.

In the preferred embodiment the RIS system or its memory or storage repository thus serves not only to store the different protocol data sets but also to secure the respective protocol content. The respective protocols and the current associations of the protocols with the respective modalities are thus centrally available on the RIS system at any time. The transparency of the system can thereby be advantageously increased.

DESCRIPTION OF THE DRAWINGS

FIG. 2 shows an example for data exchange between different nodes according to a preferred embodiment of the inventive method.

DESCRIPTION OF THE PREFERRED EMBODIMENTS

Figure 1:
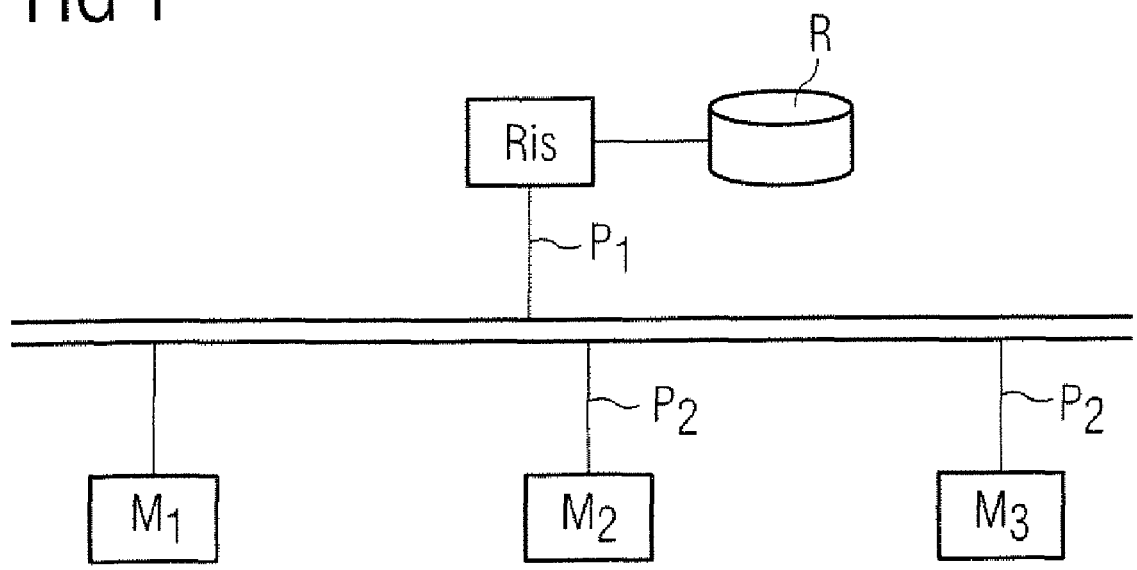
FIG. 1 is an overview representation of nodes of a radiology information system according to a preferred embodiment of the invention.

In an overview representation, FIG. 1 shows the basic design for an inventive method for provision of protocols. A number of different modalities (in particular of MR apparatuses M) are connected to a central information system (in particular to the radiology information system RIS) via a network. An RIS repository R for data retention is associated with the RIS system RIS.

The following detailed description of FIG. 1 is based on the example of MR apparatuses and the respective protocols necessary for these. The invention is not limited to this form of the modalities or apparatuses but also be applied to any other medical-technical apparatuses that must be configured by a specific configuration profile. For the current usage of the respective MR apparatuses Mi it is necessary to configure the apparatuses Mi. This typically ensues by protocols P. A protocol P typically includes a series of measurement instructions or other configurations for the apparatuses that the medical examination should implement. These can be work steps or other settings that for their part again require further steps and/or sub-steps.

In order to be able to clearly identify a protocol P, according to the invention a protocol identifier is provided that refers to the protocol content in a one-to-one relation. This is to be differentiated from the association according to which a protocol P is associated with a modality M. This association ensues through an association mechanism that associates an optimally-adapted protocol P with a modality M. There does not necessarily have to be a 1:1 relation. It is likewise possible, for example, for one and the same protocol P to be associated with a number of modalities M in the event that this reasonably should be controlled according to the same protocol workflow.

In addition to the protocol codes, the protocol contents are stored in the storage or repository R of the RIS server RIS. Access to the protocols P can ensue from all connected modalities M. In an embodiment the accesses to the protocols P can ensue only with authorization in order to avoid a data misuse.

A medical apparatus M is typically delivered with a predefined protocol P. In other words, upon delivery of the medical apparatus M there is already a predefined control scheme P, but it can be dynamically optimized and refined at a later point in time and depending on the application case. For this purpose, a specifically-designed user interface is provided using which the changes of the protocol P can be input easily and quickly.

The network connection (shown only schematically in FIG. 1) between the nodes of the information system, in particular between the central RIS server RIS and the modalities Mi, the HTTP protocol in the preferred embodiment. It is thereby with possible to also be able to integrate other applications and extensions into the system via the Internet relatively quickly and simply. Alternative embodiments provide other protocols.

The nodes shown in FIG. 1 are merely shown as examples and can be extended at any time via further instances that can be connected to the information system.

An exemplary workflow in the framework of a protocol change is explained with reference to FIG. 2.

After the first user (user 1) outputs the command that a new protocol P with regard to the apparatus M1 should be added, this command is relayed to the apparatus M1 via a user interface. The opening of a specific webpage is thereupon initiated the webpage being advantageously provided on the central RIS server RIS. After the first user has transferred an upload of the protocol file to the RIS system RIS, an update is executed on the RIS system, in particular on the repository R of the RIS server RIS.

It is possible that the central RIS system RIS requires a specification as to which modalities M the "updated" protocol P should be distributed. The user 1 then answers this question via the respective user interface and this is relayed to the RIS system RIS. The protocols P are thereupon relayed to the respective selected apparatuses Mi according to the response previously mentioned. This typically likewise ensues via the HTTP protocol. This is characterized in FIG. 2 with the command "Push Protocol P". This is thereupon converted at the apparatus M2 (which serves in FIG. 2 as an example for such an apparatus) at which the new protocol P should be imported. The conversion of the respective protocol P is an optional measure in order to adapt the respective protocol P to the specific requirements of the respective apparatus Mi.

At any point in time it is possible for a command to be output that initiates the display of new protocols P. In FIG. 2 this is exemplarily described by the second user. After output of the display command, the converted protocol is displayed via a user interface. It is possible for a user to accept the changed protocol or subjects the protocol to a further modification process again.

In the event that the new protocol P has been accepted, a corresponding communication ensues from the modality Mi to the central RIS server RIS.

After the new protocol P that has been adopted as accepted is stored in the central system, an update of the protocol distribution matrix ensues. At any point in time it is possible that a query to the RIS system RIS ensues as to which protocols P have been accepted at which modalities M. A display of the protocol distribution matrix is initiated upon this command. This typically ensues via the central RIS server RIS.

It is advantageously possible for the respective state of the protocols P to be queried at any point in time and is made transparent in a protocol distribution matrix. It is thereby possible to easily be able to track possible errors and/or incorrect associations of protocols P.

A further advantage of the inventive solution is that it can be integrated simply and quickly into already-existing radiology systems without further subsequent changes. Moreover, it can likewise be added to already-existing systems as an isolated application. A fast, easy and consistent update of protocols P from and to the central RIS server RIS can be achieved with the inventive solution and in particular with the provided association mechanisms.

Although modifications and changes may be suggested by those skilled in the art, it is the intention of the inventors to embody within the patent warranted hereon all changes and modifications as reasonably and properly come within the scope of their contribution to the art.

We claim as our invention:

1. A method for providing protocols for configuration of a medical apparatus for implementing a medical examination, comprising the steps of:
    employing a central radiology information system as a server;
    employing a plurality of medical apparatuses, for respectively implementing medical examinations, as clients of said server;
    communicating among said radiology information system and said plurality of medical apparatuses via a network;
    producing a locally-created protocol at one of said medical apparatuses by generating or amending, at said one of said medical apparatuses, an existing protocol for implementing a medical examination and relaying said locally-created protocol from said one of said medical apparatuses at least to said radiology information system;
    generating a set of protocols at said radiology information system based on said locally-created protocol from said one of said medical apparatuses for distribution to at least some of the medical apparatuses, other than said one of said medical apparatuses, in said plurality of medical apparatuses;
    at said radiology information system, applying a consistency procedure to each protocol in said set of protocols to ensure consistency and uniformity, for use by said at least some of said medical apparatuses, among the protocols in said set of protocols, as a result of said set of protocols being generated based on said locally-created protocol produced at said one of said medical apparatuses; and
    automatically electronically emitting a warning message when said consistency check indicates said consistency and uniformity do not exist.

2. A method as claimed in claim 1 comprising, in said consistency procedure, automatically electronically associating at least one of said protocols in said set of protocols with one of said medical apparatuses.

3. A method as claimed in claim 1 comprising allowing access to said network via a user interface to download or upload any of said protocols in said set of protocols.

4. A method as claimed in claim 1 comprising allowing access to said network via a user interface and, through said user interface, allowing modification of at least said one of said protocols.

5. A medical system comprising:
    a central radiology information system operating as a server;
    a plurality of medical apparatuses, for respectively implementing medical examinations, operating as clients of said server;
    one of said medical apparatuses being configured to allow a locally-created protocol to be produced at said one of said medical apparatuses by generating or amending an existing protocol at said one of said medical apparatuses;
    a network allowing communication among said radiology information system, said one of said medical apparatuses being configured to relay said locally-created protocol to said radiology information system via said network; and
    said radiology information system being configured to generate a set of protocols based on said locally-created protocol from said one of said medical apparatuses for distribution to at least some of the medical apparatuses, other than said one of said medical apparatuses, in said plurality of medical apparatuses; to apply a consistency procedure to each protocol in said set of protocols to ensure consistency and uniformity among the protocols in said set of protocols, as a result of said set of protocols being generated based on said locally-created protocol produced at said one of said medical apparatuses, and to automatically emit a warning signal when said consistency check indicates said consistency and uniformity do not exist.

6. A non-transitory computer-readable medium encoded with a data structure, said medium being loadable into a processor of a radiology information system that is connected via a network with a plurality of medical apparatuses respectively operating according to respective protocols to implement respective medical examinations, said data structure configuring said radiology information system to:

employ said central radiology information system as a server one of said medical apparatuses generating a protocol for implementing a medical examination;

employ said plurality of medical apparatuses as clients of said server;

allow one of said medical apparatuses to be operated to produce a locally-created protocol, by generating or amending an existing protocol at said one of said medical apparatuses;

communicate among said radiology information system and said plurality of medical apparatuses via a network and to relay said locally-created protocol from said one of said medical apparatuses to said radiology information system;

generate a set of protocols based on said locally-created protocol from said one of said medical apparatuses for distribution to at least some of the medical apparatuses, other than said one of said medical apparatuses, in said plurality of medical apparatuses; and apply a consistency procedure to each protocol in said set of protocols to ensure consistency and uniformity among the protocols in said set of protocols, as a result of said set of protocols being generated based on said locally-created protocol produced at said one of said medical apparatuses; and automatically emit a warning message when said consistency check indicates said consistency and uniformity do not exist.

* * * * *